US009943625B2

(12) United States Patent
Koo et al.

(10) Patent No.: US 9,943,625 B2
(45) Date of Patent: Apr. 17, 2018

(54) MAGNESIUM ALLOY

(71) Applicant: U & I CORPORATION, Gyeonggi-do (KR)

(72) Inventors: Ja-Kyo Koo, Seoul (KR); Hyun-Kwang Seok, Seoul (KR); Seok-Jo Yang, Daejeon (KR); Yu-Chan Kim, Seoul (KR); Sung-Youn Cho, Uijeongbu-Si (KR); Jong-Tack Kim, Jeonju-Si (KR)

(73) Assignee: U&I Corporation (KR)

( * ) Notice: Subject to any disclaimer, the term of this patent is extended or adjusted under 35 U.S.C. 154(b) by 0 days.

(21) Appl. No.: 15/373,538

(22) Filed: Dec. 9, 2016

(65) Prior Publication Data

US 2017/0119922 A1    May 4, 2017

Related U.S. Application Data

(62) Division of application No. 13/511,891, filed as application No. PCT/KR2010/008725 on Dec. 7, 2010, now abandoned.

(30) Foreign Application Priority Data

Dec. 7, 2009   (KR) .......................... 10-2009-0120356

(51) Int. Cl.
    *C22C 23/00*       (2006.01)
    *C22C 1/02*        (2006.01)
    (Continued)

(52) U.S. Cl.
    CPC .............. *A61L 27/047* (2013.01); *A61L 27/50* (2013.01); *C22C 1/02* (2013.01); *C22C 23/00* (2013.01)

(58) Field of Classification Search
    CPC ......... C22C 23/00; C22C 23/02; C22C 23/04; C22C 23/06; C22C 1/00; C22C 1/02;
    (Continued)

(56) References Cited

U.S. PATENT DOCUMENTS 5,304,260 A  *  4/1994  Aikawa .................. C22C 45/005
                                                    148/403
2003/0000608 A1    1/2003  Horie et al.
2008/0193652 A1    8/2008  De Figueiredo Gomes et al.

FOREIGN PATENT DOCUMENTS

JP          06-025791 A      2/1994
JP          07-018364 A      1/1995
(Continued)

OTHER PUBLICATIONS

G.C. Kuczynski et al., "Corrosion Characteristics of Some Magnesium-Zinc-Calcium Alloys", Journal of Electrochemical Society, Feb. 1948, vol. 93, No. 2, pp. 41-46.
(Continued)

*Primary Examiner* — Colleen Dunn
*Assistant Examiner* — Anthony Liang
(74) *Attorney, Agent, or Firm* — Blank Rome LLP

(57) ABSTRACT

The present invention relates to a magnesium alloy having controlled corrosion resistance properties, which comprises magnesium (Mg) and an alloying element and includes a magnesium phase and a phase composed of magnesium and the alloying element, wherein the difference in electrical potential between the magnesium phase and the phase composed of magnesium and the alloying element is greater than 0 V but not greater than 0.2 V.

4 Claims, 4 Drawing Sheets

(51) Int. Cl.
*A61L 27/04* (2006.01)
*A61L 27/50* (2006.01)

(58) Field of Classification Search
CPC .... C22C 1/03; C22C 1/08; C22C 1/10; C22C 1/1036; C22C 1/1042; C22C 1/1094; A61L 27/04; A61L 27/047; A61L 27/50
USPC .................................................. 420/411, 402
See application file for complete search history.

(56) References Cited

FOREIGN PATENT DOCUMENTS

| | | |
|---|---|---|
| JP | 2007-270159 A | 10/2007 |
| JP | 2008-194687 A | 8/2008 |

OTHER PUBLICATIONS

Erlin Zhang et al., "Microstructure, Mechanical Properties and Bio-Corrosion Properties of Mg—Zn—Mn—Ca Alloy for Biomedical Application", Materials Science and Engineering A, Dec. 5, 2008, vol. 497, No. 1-2, pp. 111-118.

J. F. Nie et al., "Precipitation Hardening of Mg—Ca(—Zn) Alloys," Scripta Materials, vol. 37, No. 10, pp. 1475-1481, 1997.

E. Zhang et al., "Microstructure, Mechanical and Corrosion Properties and Biocompatibility of Mg—Zn—Mn Alloys for Biomedical Application," Materials Science and Engineering, C 29, pp. 987-993, 2009.

* cited by examiner

[Fig. 1]
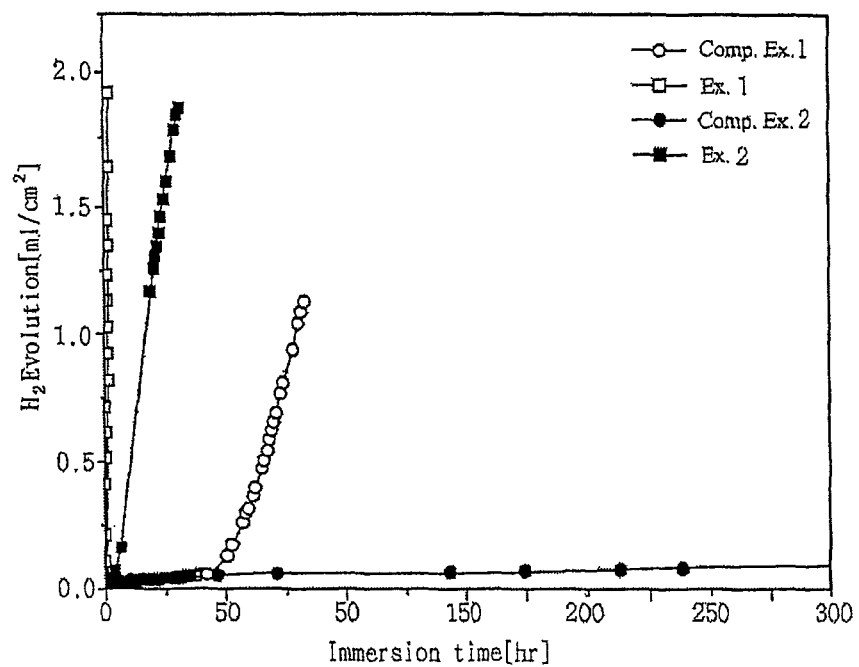
[Fig. 2]
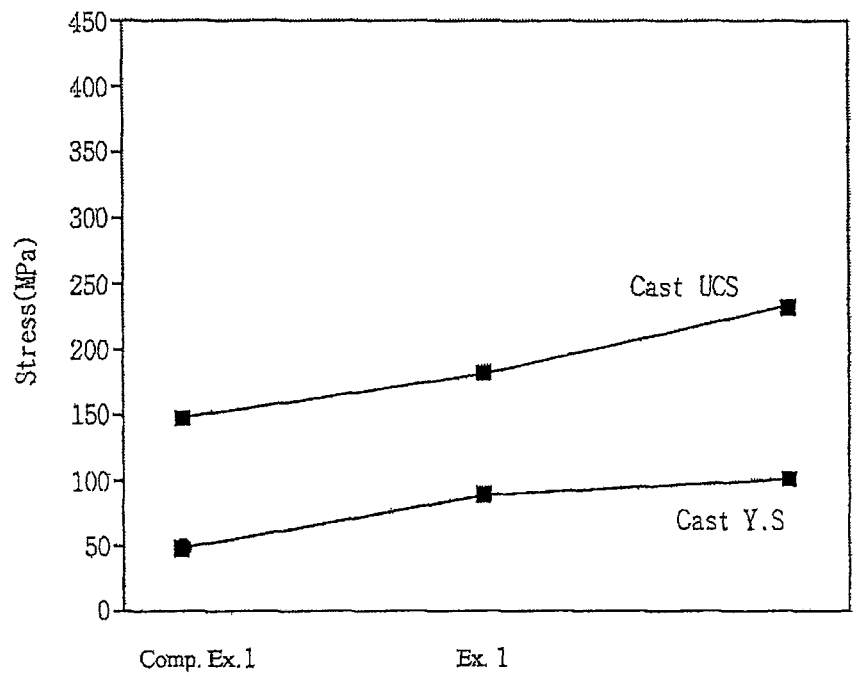

[Fig. 3]
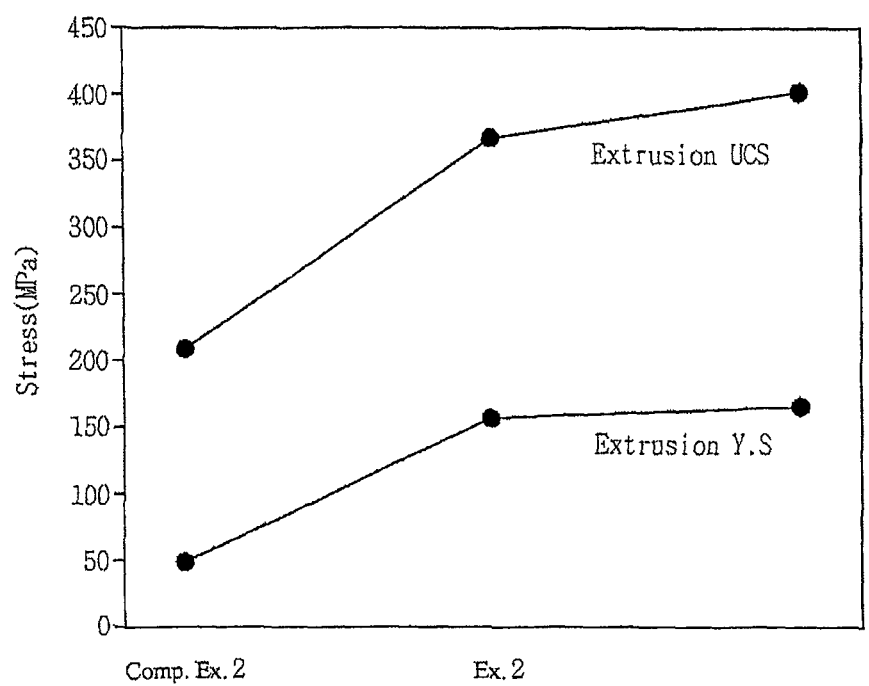

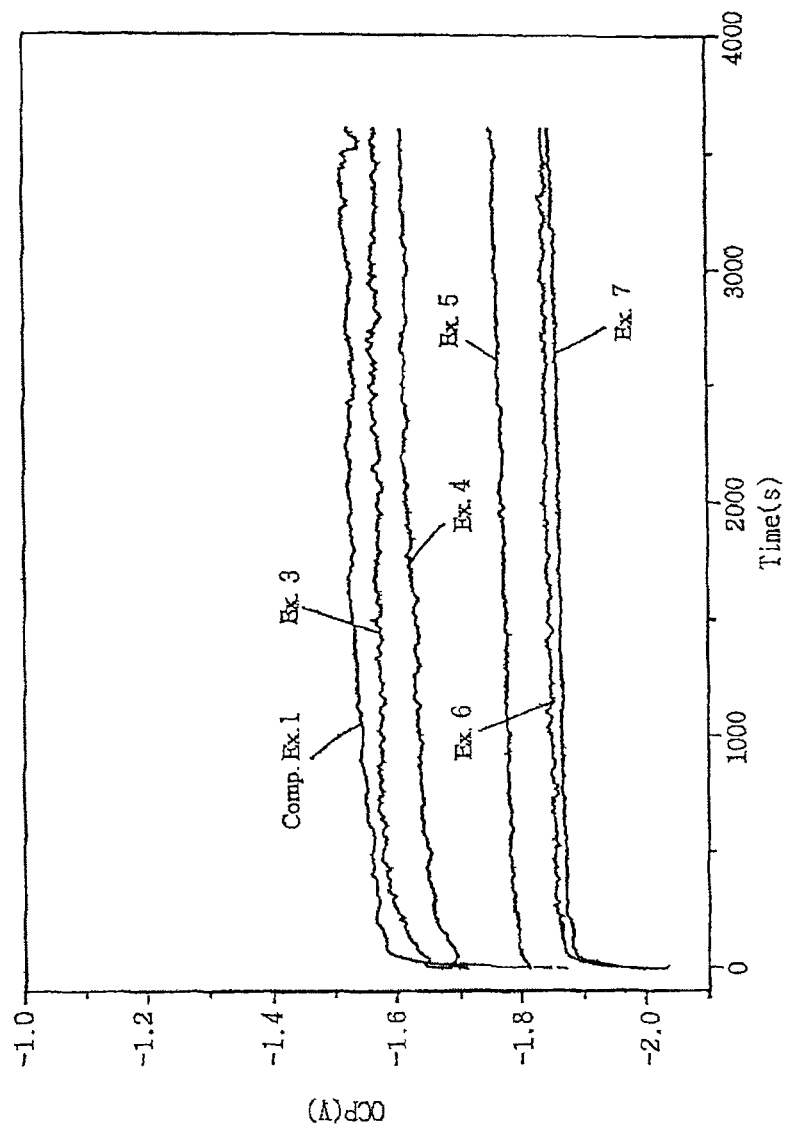
[Fig. 4]

[Fig. 5]
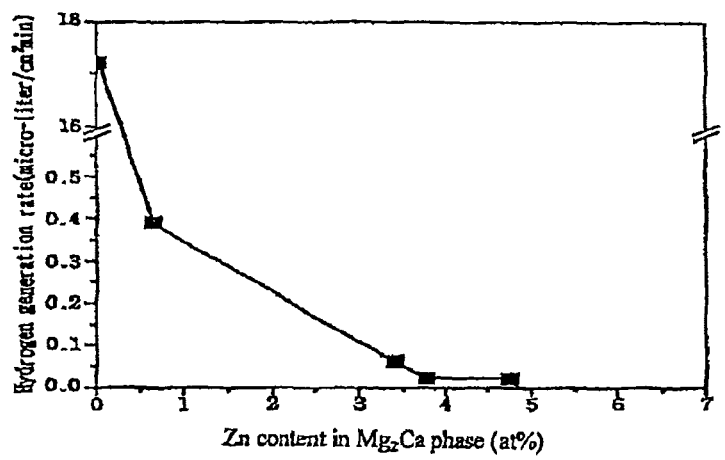
[Fig. 6]
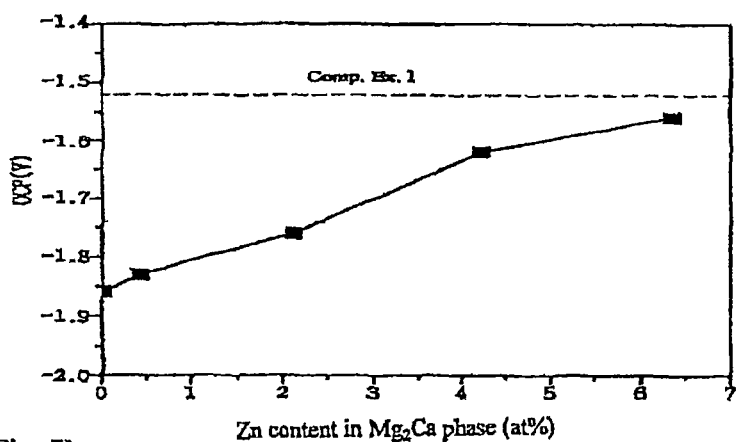
[Fig. 7]
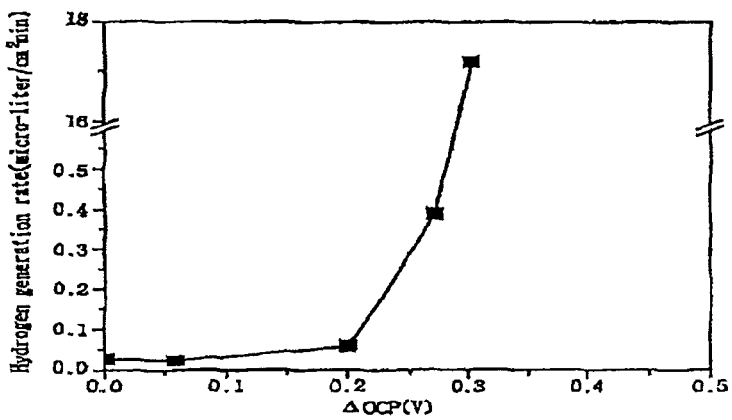

MAGNESIUM ALLOY

CROSS REFERENCE TO RELATED APPLICATION

This application is a divisional of U.S. application Ser. No. 13/511,891, filed May 24, 2012, which claims the benefit of priority of Korean Patent Application No. 10-2009-0120356, filed with the Korean Intellectual Property Office on Dec. 7, 2009, the disclosures of which are incorporated herein by reference in their entirety.

TECHNICAL FIELD

The present invention relates to a magnesium alloy.

BACKGROUND ART

Magnesium alloys are easily shaped, but have disadvantages of poor corrosion resistance and poor strength. Studies are continually performed with the aim of suitably changing the composition of magnesium alloys in order to improve the corrosion resistance and strength of magnesium alloys. In addition, studies have demonstrated that an increase in the amount of alloying elements in the magnesium alloy leads to an increase in the mechanical strength of the magnesium alloy. However, as the amount of alloying elements increases, several phases are formed, and an increase in the difference in electrical potential between these phases results in conditions such that a galvanic circuit, which increases the rate of corrosion of the alloy, is likely to be formed.

Therefore, there is a need for studies on a magnesium alloy, the corrosion resistance properties of which can be controlled and which has excellent corrosion resistance and strength.

DISCLOSURE

Technical Problem

It is an object of the present invention to provide a magnesium alloy whose corrosion resistance properties are controlled by adding an alloying element having an electrical potential different from that of magnesium, depending on the intended use of the magnesium alloy. Another object of the present invention is to provide a magnesium alloy, the corrosion resistance and strength properties of which can be controlled through post-treatment processing.

Technical Solution

In order to accomplish the above objects, the present invention provides a magnesium alloy having controlled corrosion resistance properties, which comprises magnesium (Mg) and an alloying element and includes a magnesium phase and a phase composed of magnesium and the alloying element, wherein the difference in electrical potential between the magnesium phase and the phase composed of magnesium and the alloying element is greater than 0 V but not greater than 0.2 V.

Advantageous Effects

The corrosion resistance properties of the magnesium alloy according to the present invention can be controlled using the difference in electrical potential between the magnesium and the alloying element. In addition, the corrosion resistance and strength properties of the magnesium alloy of the present invention can also be controlled through post-treatment processing. Furthermore, due to these effects, the magnesium alloy can be used in the industrial and medical fields.

DESCRIPTION OF DRAWINGS

FIG. 1 is a graphic diagram showing the corrosion rates of the magnesium alloys of Examples 1 and 2 and Comparative Examples 1 and 2.

FIG. 2 is a graphic diagram showing the results of measurement of the strengths of the magnesium alloys of Example 1 and Comparative Example 1.

FIG. 3 is a graphic diagram showing the results of measurement of the strengths of the magnesium alloys of Example 2 and Comparative Example 2.

FIG. 4 is a graphic diagram showing the open circuit potentials of the magnesium alloys of Examples 3 to 7 and Comparative Example 1 as a function of time.

FIG. 5 is a graphic diagram showing the rate of generation of hydrogen as a function of the content of zinc.

FIG. 6 is a graphic diagram showing open circuit potential (electrical potential) as a function of the content of zinc.

FIG. 7 is a graphic diagram showing the rate of degradation as a function of the difference in open circuit potential (electrical potential).

BEST MODE

Hereinafter, the present invention will be described in detail.

I. Magnesium Alloy

The present invention is directed to a magnesium alloy having controlled corrosion resistance properties, which comprises magnesium (Mg) and an alloying element and includes a magnesium phase and a phase composed of magnesium and the alloying element.

Herein, the difference in electrical potential between the magnesium phase and the phase composed of magnesium and the alloying element is greater than 0 V but not greater than 0.2 V, and is preferably close to 0. If the magnesium alloy satisfies the above-described range, it has a very low rate of degradation, and thus can be effectively used in the industrial and medical fields. In addition, the magnesium alloy has excellent corrosion resistance and strength.

The alloying element is not specifically limited, as long as the difference in electrical potential between the magnesium phase and the phase composed of magnesium and the alloying element falls within the above-described range. Examples of the alloying element include calcium (Ca), iron (Fe), manganese (Mn), cobalt (Co), nickel (Ni), chromium (Cr), copper (Cu), cadmium (Cd), zirconium (Zr), silver (Ag), gold (Au), palladium (Pd), platinum (Pt), rhenium (Re), iron (Fe), zinc (Zn), molybdenum (Mo), niobium (Nb), tantalum (fa), titanium (Ti), strontium (Sr), silicon (Si), phosphorus (P) and selenium (Se).

Meanwhile, the magnesium alloy that realizes the difference in electrical potential between the magnesium phase and the phase composed of magnesium and the alloying element is preferably represented by the following formula 1:

$$Mg_aCa_bX_c \qquad \text{[Formula 1]}$$

wherein a, b and c represent the molar fractions of the respective components, a+b+c=1, 0.5≤a<1, 0≤b≤0.4, and 0≤c≤0.4; if at least one of b and c is greater than 0, and c is 0, the content of Ca is 5-33 wt % based on the total weight of the magnesium alloy; and X is one or more selected from among zirconium (Zr), molybdenum (Mo), niobium (Nb), tantalum (Ta), titanium (fi), strontium (Sr), chromium (Cr), manganese (Mn), zinc (Zn), silicon (Si), phosphorus (P), nickel (Ni) and iron (Fe).

Even if X represents two or more elements, the total molar fraction of the elements of X satisfies the range of c. As the contents of Ca and X increase, the strength of the magnesium alloy increases while the rate of degradation thereof also increases. Thus, the amounts of Ca and X in the magnesium alloy of the present invention can be determined within the above-described ranges by taking into consideration the required strength of the alloy and the rates of degradation of the additional metals.

When nickel (Ni) is included in X, nickel reduces the toxicity of the magnesium alloy and makes it possible to control the rate of corrosion of the magnesium alloy. Herein, the content of nickel is preferably 100 ppm or less, and more preferably 50 ppm or less. In addition, when iron (Fe) is included in X, iron significantly influences the increase in the rate of corrosion of the magnesium, and for this reason, the content of iron is preferably 1,000 ppm or less, and more preferably 500 ppm or less. If iron is contained in an amount exceeding the upper limit of the above range, iron will be present as an independent factor, without being fixed to magnesium, thus increasing the rate of corrosion of the magnesium alloy.

The magnesium alloy that realizes the difference in electrical potential between the magnesium phase and the phase composed of magnesium and the alloying element is preferably represented by the following formula 2.

The magnesium alloy represented by formula 2 comprises, based on the total weight thereof, greater than 0 wt % but not greater than 23 wt % of calcium (Ca), greater than 0 wt % but not greater than 10 wt % of Y, and the balance of magnesium (Mg).

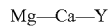

Mg—Ca—Y [Formula 2]

wherein Y is Mn or Zn.

When the composition of the magnesium alloy represented by formula 2 falls within the above-described ranges, it has not only improved mechanical properties, but also improved corrosion resistance, and does not undergo brittle fracture.

The magnesium alloy represented by formula 2 preferably comprises, based on the total weight thereof, greater than 0 wt % but not greater than 23 wt % of calcium (Ca), 0.1-5 wt % of Y, and the balance of magnesium (Mg). More preferably, the magnesium alloy represented by formula 2 comprises greater than 0 wt % but not greater than 23 wt % of calcium (Ca), 0.1-3 wt % of Y, and the balance of Mg. The reason for this is that when the same corrosion rate is realized, taking into consideration the possible side effects of impurities, the contents of the impurities should preferably be low.

The magnesium alloy that realizes the difference in electrical potential between the magnesium phase and the phase composed of magnesium and the alloying element is preferably represented by the following formula 3. The magnesium alloy represented by formula 3 comprises, based on the total weight thereof, greater than 0 wt % but no greater than 40 wt % of Z and the balance of magnesium (Mg).

Mg—Z [Formula 3]

wherein Z is one or more selected from among manganese (Mn), cobalt (Co), nickel (Ni), chromium (Cr), copper (Cu), cadmium (Cd), zirconium (Zr), silver (Ag), gold (Au), palladium (Pd), platinum (Pt), rhenium (Re), iron (Fe), zinc (Zn), molybdenum (Mo), niobium (Nb), tantalum (Ta), titanium (Ti), strontium (Sr), silicon (Si), phosphorus (P) and selenium (Se). The magnesium alloy is preferably subjected to surface treatment. The surface treatment is preferably shot peening.

The magnesium alloy which is included in an implant of the present invention may be subjected to surface coating. When the surface coating is performed, a corrosion-resistant product can be produced on the surface of the magnesium alloy, whereby the rate of degradation of the magnesium alloy can be delayed.

The surface coating may be performed with a ceramic and/or polymer material.

Hereinafter, the coating of the magnesium alloy surface with a ceramic material will be described. When the magnesium is immersed in a biomimetic solution or physiological saline, the surface of the magnesium alloy can be coated with a corrosion-resistant product. Herein, the corrosion-resistant product may be a ceramic material, in which the ceramic material may be magnesium oxide or calcium phosphate. In addition, after the surface of the biodegradable magnesium alloy is coated with the corrosion-resistant product, it may further be coated with a polymer. Examples of the polymer which may be used in the present invention are as described below.

The polymer that is used to coat the surface of the magnesium alloy is not specifically limited, as long as it is one that is conventionally used in the art. Preferred examples of the polymer for use in the present invention include poly(L-lactide), poly(glycolide), poly(DL-lactide), poly(dioxanone), poly(DL-lactide-co-L-lactide), poly(DL-lactide-co-glycolide), poly(glycolide-co-trimethylene carbonate), poly(L-lactide-co-glycolide), poly(e-caprolactone), and combinations thereof.

The magnesium alloy according to the present invention can be used in various ways. For example, it may be coated on the surface of ceramic, metal and polymer materials. In addition, the magnesium alloy according to the present invention may be used in combination with a ceramic or polymeric material.

II. Preparation Method

The present invention also provides a method for preparing a magnesium alloy having controlled corrosion resistance properties, the method comprising adding, to a magnesium alloy comprised of magnesium and an alloying element, a third element, thereby reducing the difference in electrical potential between the magnesium phase and the phase composed of magnesium and the alloying element to greater than 0 V, but not greater than 0.2 V. Herein, the magnesium alloy is preferably an alloy comprising magnesium and calcium. In addition, the third element is preferably zinc.

III. Method for Preparing Magnesium Alloy

The inventive method for preparing the magnesium alloy having controlled corrosion resistance properties may comprise the steps of: a) providing the magnesium alloy; and b) shaping the magnesium alloy.

Step a) of the method is preferably performed by melting the magnesium.

More specifically, step a) may be performed by melting the magnesium in a vacuum atmosphere or in an atmosphere of inert gas such as argon (Ar), which does not react with magnesium. In addition, step a) may be performed by melting the magnesium using various methods, such as a resistance heating method, in which heat is generated by electrically heating a resistive material, an induction heating method, in which a current is allowed to flow through an induction coil, or a method that uses a laser or focused light. Among these melting methods, the resistance heating method is the most economical method. In addition, the melted alloy (hereinafter referred to as the "melt") is preferably stirred during the melting of magnesium such that impurities can be mixed well.

Step b) of the inventive method for preparing the magnesium alloy may be performed by shaping the molten magnesium alloy using one or more selected from the group consisting of a quenching method, an extrusion method, and a metal processing method. The quenching method can be used in order to improve the mechanical strength of the magnesium alloy. More specifically, if magnesium is melted in step a), a method of immersing a crucible containing the molten magnesium in water may be used. In addition, a quenching method of spraying inert gas such as argon onto the molten magnesium may also be used. This spray quenching method can quench the molten magnesium at a very high quenching rate, thereby realizing a very fine structure. However, in the case in which magnesium is cast in a small size, it should be noted that a plurality of pores (black portions) can also be formed.

The extrusion method is used to make the structure of the magnesium uniform and enhance the mechanical performance of the magnesium. The extrusion method can control the strength and corrosion resistance properties of the magnesium alloy of the present invention.

The extrusion method is preferably performed at 30~450° C. Furthermore, the extrusion of magnesium may be carried out at a ratio of reduction in the cross-sectional area before and after extrusion (an extrusion ratio) of 10:1 to 30:1. As the extrusion ratio increases, the fine structure of the extruded material becomes more uniform, and defects formed during casting are easily removed. In this case, it is preferred to increase the capacity of the extrusion system.

The metal processing method is not particularly limited so long as it is known in the art. Examples of the metal processing method include a method in which the molten magnesium is poured and cast in a mold that is processed such that it has a shape close to the shape of a final product; a method in which the molten magnesium is prepared into an intermediate material such as a rod or a sheet and is then subjected to turning or milling; and a method in which the magnesium alloy is forged at a higher pressure, thus obtaining a final product.

Mode for Invention

Hereinafter, the preparation of magnesium alloys will be described in further detail with reference to examples. It is to be understood, however, that these examples are provided for illustrative purposes only, and are not intended to limit the scope of the present invention.

Examples 1 to 2 and Comparative Examples 1 and 2: Preparation of Magnesium Alloys Example 1 and Comparative Example Elements were mixed to have the compositions shown in Table 1 below, and were charged into a stainless steel (SUS 410) crucible having an inner diameter of 50 mm. Then, while argon (Ar) gas was allowed to flow around the crucible so that the magnesium in the crucible did not come into contact with air, the temperature of the crucible was increased to about 700~750° C. using a resistance heating furnace, thereby melting the magnesium. The crucible was shaken so that the molten magnesium could be mixed well with the impurities. The completely molted Mg alloy was quenched, thus preparing solid-state magnesium. Also, upon quenching, the crucible was immersed in water (20° C.) to enhance the mechanical strength of magnesium such that the molten magnesium was rapidly quenched, thereby preparing a magnesium alloy.

TABLE 1

| | Mg (parts by weight) | Ca (parts by weight) | Zn (parts by weight) | Difference in electrical potential (V) Mg vs. Mg—Ca—Zn |
|---|---|---|---|---|
| Example 1 | 95 | 5 | 0 | —(due to the absence of Zn) |
| Comparative Example 1 | 100 | — | — | — |

Mg: Ultrahigh purity (99.98%) for reagents

Example 2 and Comparative Example 2

The magnesium alloys of Example 1 and Comparative Example 1 were extruded. The extrusion was performed at 370~375° C., and the ratio of reduction in the cross-sectional area before and after extrusion (the extrusion ratio) was set at 15:1. Herein, the extruded alloy of Comparative Example 2 corresponds to the magnesium alloy of Comparative Example 1.

Test Example 1: Evaluation of Rate of Corrosion of Magnesium Alloy

In general, the rate of corrosion of magnesium alloys is determined by measuring the amount of hydrogen generated when the magnesium alloy is immersed in the solution shown in Table 2 below. This is because the biodegradation of magnesium results in the generation of hydrogen and the solution shown in Table 2 is a biomimetic solution.

TABLE 2

| | Molar concentration (mM/L) | Mass (g) |
|---|---|---|
| $CaCl_2 2H_2O$ | 1.26 | 0.185 |
| KCl | 5.37 | 0.400 |
| $KH_2PO_4$ | 0.44 | 0.060 |
| $MgSO4\ 7H2O$ | 0.81 | 0.200 |
| NaCl | 136.89 | 8.000 |
| $Na2HPO_4\ 2H_2O$ | 0.34 | 0.060 |
| $NaHCO_3$ | 4.17 | 0.350 |
| D-Glucose | 5.55 | 1.000 |

FIG. 1 is a graphic diagram showing the rates of corrosion of the magnesium alloys of Examples 1 to 2 and Comparative Examples 1 and 2.

As can be seen in FIG. 1, the corrosion resistance properties of the magnesium alloys were significantly improved when the alloying element was added and extrusion was performed. This suggests that the rate of degradation of magnesium alloys can be controlled to various levels using an alloying element and a post-treatment process.

Test Example 2: Evaluation of Strength of Magnesium Alloys

The magnesium alloys of Examples 1 to 2 and Comparative Examples 1 and 2 were electric-discharge-machined into specimens having a diameter of 3 mm and a length of 6 mm. The upper and lower surfaces of the specimens were polished with #1000 emery paper to adjust the level of the surface. The specimens were horizontally placed on a jig made of tungsten carbide, and then a force was vertically applied to the specimens using the head of a compression tester with a maximum load of 20 tons. At this time, the vertical speed of the head was $10_4$/s. During the test, the changes in strain and compressive stress were recorded in real time using an extensometer and a load cell provided in the compression tester. At this time, the size of the specimen was too small to place the extensometer in the specimen, so the extensometer was placed in the jig of the tester that was used to press the specimen. Therefore, the strain of the specimen was measured as higher than its actual strain.

FIG. 2 is a graphic diagram showing the results of measurement of the strengths of the magnesium alloys of Example 1 and Comparative Example 1. FIG. 3 is a graphic diagram showing the results of measurement of the strengths of the magnesium alloys of Example 2 and Comparative Example 2.

In addition, Table 3 below shows the strengths of the magnesium alloys of Examples 1 to 2 and Comparative Examples 1 and 2. In Table 3, Y.S indicates yield strength, and UCS indicates ultimate compression strength.

TABLE 3

| | | Example 1 | Example 2 | Comp. Example 1 | Comp. Example 2 |
|---|---|---|---|---|---|
| Strength (MPa) | Y.S | 87 | 155 | 47 | 48 |
| | UCS | 180 | 365 | 146 | 208 |

As can be seen in FIGS. 2 and 3 and Table 3, the strength properties of the magnesium alloys were significantly improved when the alloying element was added and physical treatment was performed.

From the results in FIGS. 1 to 3, it can be seen that the magnesium alloys of Examples 1 to 2 according to the present invention can be controlled to have corrosion resistance properties ranging from 2-3 days to 2 years and strengths of 87 MPa to 400 MPa by controlling the composition of the alloy and performing the post-treatment processing (extrusion). Thus, it can be seen that a magnesium alloy that can maintain its strength for a required period of time can be prepared based on the above findings.

Examples 3 to 7: Preparation of Magnesium Alloys

Magnesium alloys of Examples 3 to 7 were prepared using the compositions shown in Table 4 below according to the method of Example 1.

TABLE 4

| | Example 3 | Example 4 | Example 5 | Example 6 | Example 7 |
|---|---|---|---|---|---|
| Mg$_2$Ca (wt %) | 93.65 | 95.78 | 97.89 | 99.58 | 100 |
| Zn (wt %) | 6.35 | 4.22 | 2.11 | 0.42 | 0 |

Test Example 3: Evaluation of Open Circuit Potentials

FIG. 4 is a graphic diagram showing the open circuit potentials of the magnesium alloys of Examples 3 to 7 and Comparative Example 1 as a function of time.

As can be seen in FIG. 4, the magnesium alloys of Comparative Example 1 and Example 3 showed the smallest difference in open circuit potential, indicating the best corrosion resistance, but the magnesium alloys of Comparative Example 1 and Example 7 showed a great difference in open circuit potential, indicating the highest corrosion rate.

Test Example 4: Evaluation of Rate of Biodegradation by Difference in Electrical Potential The corrosion rates of the magnesium alloys were determined by measuring the amount of hydrogen that was generated when the magnesium alloys were immersed in the solution of Table 2 above.

FIG. 5 is a graphic diagram showing the rate of generation of hydrogen as a function of the content of zinc. In FIG. 5, the x-axis indicates the Zn (at %) content in Mg$_2$Ca phase.

As can be seen in FIG. 5, as the content of zinc increased, the rate of corrosion of the magnesium alloys increased.

FIG. 6 is a graphic diagram showing the open circuit potential (electrical potential) as a function of the content of zinc. In FIG. 6, the x-axis indicates the Zn (at %) content in Mg$_2$Ca phase.

As can be seen in FIG. 6, as the content of zinc increased, the difference in open circuit potential from Comparative Example 1 decreased.

FIG. 7 shows the rate of degradation of a magnesium alloy as a function of the difference in open circuit potential.

As can be seen in FIG. 7, when the difference in open circuit potential was greater than 0.2 V, the rate of degradation of the magnesium alloy rapidly increased. In FIG. 7, the rate of degradation is expressed as hydrogen generation rate.

The invention claimed is:

1. An extruded magnesium alloy for forming a medical implant, comprising greater than 0 wt % but not greater than 23 wt % of calcium (Ca), greater than 0 wt % but not greater than 10 wt % of zinc (Zn), and a balance of magnesium (Mg) and inevitable impurities; and said magnesium alloy includes a magnesium phase and a Mg$_2$Ca phase, wherein a difference in electrical potential between the magnesium phase and the Mg$_2$Ca phase is greater than 0 V but not greater than 0.2 V, when measured in a biomimetic solution; wherein Mg$_2$Ca phase contains Zn between 4.22 and 6.35 wt %, and wherein the biomimetic solution has a composition which is represented by the following [Table 1].

TABLE 1

| | Molar concentration (mM/L) | Mass (g) |
|---|---|---|
| CaCl$_2$ 2H$_2$O | 1.26 | 0.185 |
| KCl | 5.37 | 0.400 |
| KH$_2$PO$_4$ | 0.44 | 0.060 |
| MgSO$_4$ 7H$_2$O | 0.81 | 0.200 |
| NaCl | 136.89 | 8.000 |
| Na$_2$HPO$_4$ 2H$_2$O | 0.34 | 0.060 |
| NaHCO$_3$ | 4.17 | 0.350 |
| D-Glucose | 5.55 | 1.000. |

2. The magnesium alloy of claim 1, wherein the magnesium alloy comprises greater than or equal to 5 wt % and not greater than 23 wt % of calcium (Ca), greater than or equal to 0.1 wt % and not greater than 5 wt % of zinc (Zn), a balance of magnesium (Mg) and inevitable impurities.

3. The magnesium alloy of claim 1, wherein the magnesium alloy is surface-treated.

4. A method for preparing a magnesium alloy for forming a medical implant, the method comprising adding, to a magnesium alloy comprising greater than 0 wt % but not greater than 23 wt % of calcium (Ca) and a balance of magnesium (Mg) and inevitable impurities, a third alloying element, thereby reducing the difference in electrical potential between a magnesium phase and a $Mg_2Ca$ phase to greater than 0 V but not greater than 0.2 V, when measured in a biomimetic solution, and extruding the magnesium alloy, wherein the third alloying element is Zn, wherein the $Mg_2Ca$ phase contains Zn in weight % between 4.22 and 6.35, and wherein the biomimetic solution has a composition which is represented by the following [Table 1].

TABLE 1

|  | Molar concentration (mM/L) | Mass (g) |
|---|---|---|
| $CaCl_2\ 2H_2O$ | 1.26 | 0.185 |
| KCl | 5.37 | 0.400 |
| $KH_2PO_4$ | 0.44 | 0.060 |
| $MgSO_4\ 7H_2O$ | 0.81 | 0.200 |
| NaCl | 136.89 | 8.000 |
| $Na_2HPO_4\ 2H_2O$ | 0.34 | 0.060 |
| $NaHCO_3$ | 4.17 | 0.350 |
| D-Glucose | 5.55 | 1.000. |

\* \* \* \* \*